May 26, 1942. M. H. HORVATH Plant Pat. 518
ROSE
Filed Oct. 28, 1941
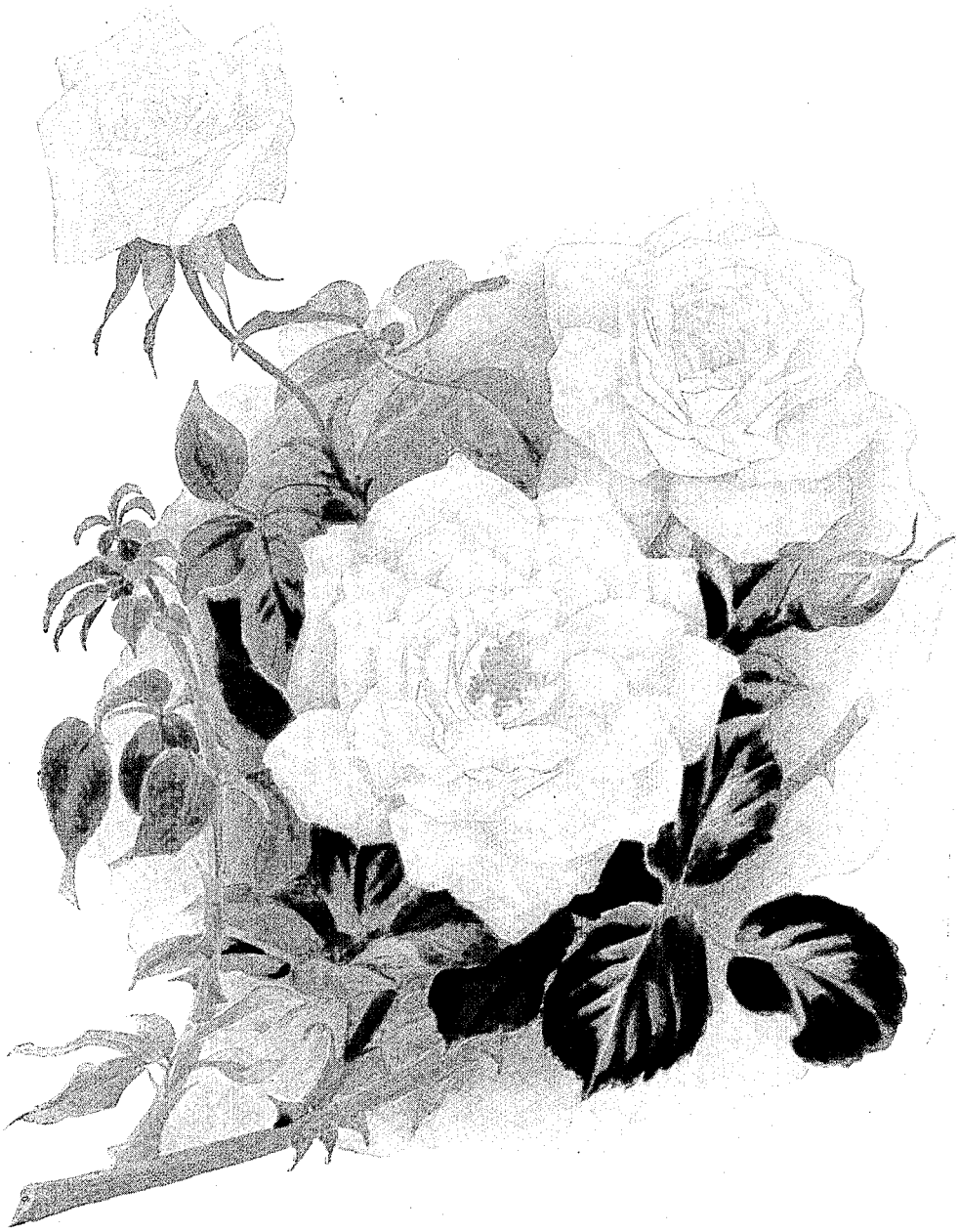
WITNESS
Addison E. Avery
INVENTOR
MICHAEL H. HORVATH
BY John H. Leonard, his ATTORNEY Patented May 26, 1942

UNITED STATES PATENT OFFICE

518

ROSE

Michael H. Horvath, Mentor, Ohio

Application October 28, 1941, Serial No. 416,832

1 Claim. (Cl. 47—61)

This invention relates to a new variety of rose which is a large flowered climbing *rosa setigera* hybrid.

The variety was originally produced by crossing an unnamed seedling, as the female, or seed, parent, with the hybrid tea rose "Golden Dawn" as the male, or pollen, parent. The unnamed seedling used as the female, or seed, parent resulted from a cross between a *rosa setigera* hybrid and the hybrid tea rose "Butterfly."

The new variety was asexually reproduced by me beginning in 1935 at my test fields at Mentor, Ohio, and has been asexually reproduced continuously since 1935 at my test fields and in the nursery of Wayside Gardens Company, at Mentor, Ohio, the reproduction being by budding.

The variety has a very strong constitution. Its resistance to mildew and black spot are exceptional, in fact, as far as is known, it is immune to mildew and black spot and the other common rose maladies. Its winter resistance is above the average of the so-called hardy climbers and it has withstood sub-zero temperatures without any damage. It endures most soil conditions and thrives in any ordinary fertile soil.

The plant in general is bushy from the ground up and is well filled out. It grows to a height of ten to twelve feet or more, its growth being very vigorous. It also endures drought and wet seasons well and does well under the normal conditions of sun, shade, and the like. The main stalks are upright and curving with a tendency toward drooping at their outer ends. They are heavily branched and relatively stiff and tough for this type of plant and are adequate to support the foliage and bloom well. The color of the new growth is generally light green, this coloring merging into a reddish green comparable to withered rose or Korea, Maerz & Paul Plate No. 5–J–10 and 11 toward the outer ends of the new growth and particularly on the leaf stalks on the outer ends of the new growth. The branching is generally alternate, the branches being generally smooth. The foliage is compact, the leaves being abundant in quantity and arranged in the usual manner. The new leaves on the new growth range from meadow pink, comparable to Maerz & Paul Plate No. 5–C–5, to withered rose, or Korea, comparable to Maerz & Paul Plate No. 5–J–10 and 11, on the upper surface, and are a meadow pink, comparable to Maerz & Paul Plate No. 5–C–5, on the under surface. On both the newer growth and the older growth, the new leaves range in color from a grass green, comparable to Maerz & Paul Plate No. 21–L–5, to cress green and peridot, comparable respectively to Maerz & Paul Plate Nos. 22–K–6 and 22–L–6, on the upper surface, and a lighter green on the under surface. The older leaves are a cerro green, comparable to Maerz & Paul Plate No. 22–L–5 on the upper surface and a lighter green on the under surface.

An important feature of the foliage is that the leaves, particularly on the older growth, have a silicious coating giving them a somewhat glossy appearence. It is believed that it is this coating which renders the leaves so highly resistant or immune to mildew, black spot, and other diseases which would attack the leaves. The leaves vary in size from large to medium and are generally ovate with acute apices and serrated margins. They are coriaceous, relatively thick, and smooth and glossy on the upper surfaces. The leaf stalks, and often substantial adjacent portions of the stems, approximate the color of the associated leaves on the newer growth, and on many of the green leaves as well as the meadow pink leaves, the meadow pink color of the stalks continues frequently along the main rib and veins of the leaves. The leaf stems average five to six inches long and are strong, smooth and glabrous.

The plant has stood severe winters in northern Ohio and prefers the usual conditions for roses. It does exceptionally well in well-drained clay coil in which the clay content is 60 to 85%.

The plant blooms continuously from early June to the middle of July and under favorable conditions is recurrent for a longer period.

The buds are about normal for a plant of this general type, being of medium size, conical in shape, with a spherical base, and supported generally upright or in a slightly leaning position.

The color of the flower when the spals first divide is a bright salmon pink and when the sepals begin to unfurl the color graduates to a sun-glow pink, comparable to Maerz & Paul Plate No. 2–J–10, this latter color continuing until the flower is about half-blown. When the flower is half-blown, its color ranges from sun-glow pink comparable to Maerz & Paul Plate No. 2–J–10, through conch shell, comparable to Maerz & Paul Plate No. 1–D–10 to a lighter shade which is almost a safrano pink, comparable to Maerz & Paul Plate No. 1–C–9. When the flower is about two-thirds blown, its color ranges from close to a grenadine red, comparable to Maerz & Paul Plate No. 1–D–11, at the center, through approximatel ceres pink, comparable to Maerz & Paul Plate No. 2–A–9, at the outer petals and on the margins of the petals generally. When the flower is full blown, its color ranges from polar bear, comparable to Maerz & Paul Plate No.

9–B–2, to almost white, comparable to Maerz & Paul Plate No. 1–A–1, there being a decided Pinard yellow area at the base of the petals, comparable to Maerz & Paul Plate No. 9–J–1. The peduncles are of average length, smooth and irregularly prickled. They are strong and light green in color. The pedicels are likewise smooth and slightly irregularly prickled and are generally light green in color. They are strong and support the flower well.

The buds are slow in opening and finally open into a bloom from three to four inches in diameter. The plant appears to have about the average number of blooms for a well-filled plant, these blooms being borne singly and in clusters of three on laterals which are ten to twelve inches long. The resultant flowers have high centers and their permanence on the plant is good, and as cut flowers, is above average. The substance of the flower petals is very unusual and they do not crush with ordinary commercial and domestic handling. They withstand adverse weather and high winds without damage to an extent greater than other roses. The fragrance of the variety is delightful, almost spicy, and very intense. The general tonality of the blooms from a distance is creamy with a tendency toward pink and there appear to be no changes in color during the blooming season. The petals are smooth, tough, and thick, slightly curved with recurvent outer margins which gives them a distinct pointed appearance. They are imbricated in arrangement. The flowers are substantially the perfect shape of hybrid tea roses, having high centers, with from four to eight petaloids in the center.

The drawing further illustrates the characteristics of the variety and the following tabulation is a detailed description of the new variety:

*General*

Parentage:
- *Seed parent.*—Unnamed seedling resulting from a cross between a setigera hybrid and "Butterfly," a hybrid tea rose.
- *Pollen parent.*—"Golden Dawn," hybrid tea rose.

Classification:
- *Botanic.*—Setigera hybrid.

*Flower*

Blooming habit:
- *Location where observations were made.*—Trial field of Michael H. Horvath, Mentor, Ohio; trial fields of Wayside Gardens Company, Mentor, Ohio.
- *Flowering.*—Early June to middle of July, blooming continuously during the period, and under favorable conditions, recurrent.

Bud:
- *Size.*—Medium.
- *Form.*—Conical with spherical or globular base.
- *Color.*—When sepals first divide—salmon pink. When petals begin to unfurl—sunglow, comparable to Maerz & Paul Plate No. 2–J–10. When half blown—ranges from grenadine red, comparable to Maerz & Paul Plate No. 1–D–11, through approximately ceres, comparable to Maerz & Paul Plate No. 9–D–8, to a color close to peach bloom, comparable to Maerz & Paul Plate No. 2–A–9.
- *Sepals.*—Normal, smooth, long and pointed, curled at the ends, and light green.
- *Calyx.*—Shape—regular. Size—medium. Aspect—smooth and uniform. Odor when rubbed—slight rose fragrance.
- *Peduncle.*—Length—from three to six inches. Aspect—smooth and slightly and irregularly prickled. Color—light green. Strength—strong.
- *Opening.*—Slow and not much affected by weather conditions.

Bloom:
- *Size.*—Three to four inches in diameter.
- *Borne.*—Singly and in threes.
- *Stems.*—Upright and strong.
- *Form.*—When first opened—semi-globular, slightly elongated, and tapering slightly toward the top.
- *Permanence.*—On the plant—good throughout the blooming period, and when cut, above the average.

Petalage:
- *Number of petals under normal conditions.*—Forty to fifty.
- *Color.*—Center of flower, when fully opened—from a polar bear pink, Maerz & Paul Plate No. 9–B–2, to almost white, comparable to Maerz & Paul Plate No. 1–A–1, with a decided Pinard yellow at the base of the petals, comparable to Maerz & Paul Plate No. 9–J–1, with grenadine red, comparable to Maerz & Paul Plate No. 1–D–11, toward the base of the petals near the center of the flower.
- *Variegations.*—General tonality of the flower is creamy with a tendency toward pink, the color being constant during the entire blooming period.
- *Discoloration.*—At the end of the first day—none. At the end of the second day—none. At the end of the third day—none.

Petals:
- *Texture.*—Smooth, tough, and thick.
- *Appearance.*—Inside—from sun-glow, comparable to Maerz & Paul Plate No. 2–J–10, in the partly opened flower, on through a range hereinbefore set forth to almost white, comparable to Maerz & Paul Plate No. 1–A–1.
- *Form.*—Semi-globular with smoothly recurvant margins, defining pronounced points at the outer ends of the petals.
- *Arrangement.*—Imbricated to the center.
- *Petaloids in center.*—From four to eight.
- *Persistence.*—Exceptional, cut or uncut.
- *Fragrance.*—Slight tea rose, almost spicy.
- *Nature.*—Extremely tough and resistant to crushing.
- *Lasting quality.*—On plant—good. As a cut flower—exceptional.

Genital organs:
- *Stamens.*—Normal.
- *Color.*—Yellow.
- *Arrangement.*—Regular and abundant.
- *Filaments.*—Medium.
- *Color.*—White.
- *Pollen.*—Yellow.
- *Styles.*—Normal or average.
- *Stigmas.*—Normal or average.
- *Ovaries.*—Medium.

Fruit:
- *Variety.*—Medium to large.
- *Form.*—Distinctively spherical.
- *Aspect.*—Smooth.
- *Color at maturity.*—Yellow.
- *Sepals.*—Average.

*Plant*

Form: A large flowered climber.
Growth: Vigorous—from ten to twelve feet.
Foliage: Compact, closely set.
*Size.*—Medium to large.
*Quantity.*—Abundant.
*Color.*—New foliage on new growth, upper side, withered rose or Korea, comparable to Maerz & Paul Plate Nos. 5–J–10 and 11, to approximately meadow pink, comparable to Maerz & Paul Plate No. 5–C–5. Under side—approximately the same, slightly lighter. New foliage, old stalks: upper side—grass green, comparable to Maerz & Paul Plate No. 21–L–5, to cress green, comparable to Maerz & Paul Plate No. 22–K–6, and cerro green and peridot, comparable to Maerz & Paul Plate Nos. 22–L–5 and 22–L–6. Under side: approximately the same—somewhat lighter. Old foliage, old stalk—from cress green and peridot, comparable to Maerz & Paul Plate Nos. 22–K–6 and 22–L–6, to deep green, ranging from Maerz & Paul Plate Nos. 24–L–1 to 24–L–12.
*Shape.*—Generally ovate with acute apices and serrate margins.
*Texture.*—Upper side—heavy, coriaceous, with a silicious coating. Under side—normal. *Ribs and veins*—distinct, with a tendency toward withered rose or Korea, comparable to Maerz & Paul Plate Nos. 5–J–10 and 11, respectively, to meadow pink, comparable to Maerz & Paul Plate No. 5–C–5, in the rib.
*Edge.*—Serrated with regular serrations.
*Rachis.*—Medium length and generally smooth with occasional slight prickles. *Color*—green.
*Stipules.*—Smooth, generally rectangular with sharp outward points at their upper ends.
*Disease resistance.*—Exceptional—believed to be immune to the usual rose maladies.
Wood:
*Newest wood.*—Color—approximately meadow pink, comparable to Maerz & Paul Plate No. 5–C–5, to grass green, comparable to Maerz & Paul Plate No. 21–L–5. *Bark*—on newer growth—smooth.
*Old wood.*—*Color*—romantic green, comparable to Maerz & Paul Plate No. 14–L–4. *Bark*—smooth.
Thorns:
*Quantity.*—On main stalk from base—average but somewhat unevenly distributed. On laterals—average but somewhat unevenly distributed with a tendency toward a greater number near the upper ends.
*Form.*—Moderately wide base and a downward slope with substantially straight unhooked points.
*Color.*—Withered rose or Korea, comparable to Maerz & Paul Plate Nos. 5–J–10 and 11, respectively, on the younger growth, and approximately hazel, comparable to Maerz & Paul Plate No. 13–I–10, on the older growth.
*Position.*—Unevenly distributed on main stalks, laterals, and under side of leaf stalks.
*Quality.*—Strong and stiff.
*Prickles.*—None.
*Short needles.*—None.

The plant is distinct in the quality, size and appearance of the blooms, which seem to combine the best features of hybrid tea roses. The well pointed shape of the petals, their color and delicacy, and their toughness, are very unusual.

The hardiness of the plant and the silicious coating of the foliage are likewise distinctive characteristics.

Having now fully shown and described my new variety of rose and the method of its production, what I claim and desire to secure by Letters Patent of the United States is:

A variety of climbing *rosa setigera* hybrid as herein shown and described and characterized particularly by the large size, shape and color of the flower; the shape, color, toughness and quality of the petals; the resistance of the plant and foliage to disease and its practical immunity to black spot, mildew, and other rose maladies; the silicious coating of the foliage; and the delightful fragrance of the bloom.

MICHAEL H. HORVATH.